United States Patent [19]

Coffey et al.

[11] Patent Number: 5,312,436
[45] Date of Patent: May 17, 1994

[54] SUTURE FOR USE IN ENDOSCOPIC SURGERY

[76] Inventors: William R. Coffey, 7754 N. Whittier Pl., Indianapolis, Ind. 46250; Arthur C. Coffey, 5934 Crittenden Ave., Indianapolis, Ind. 46220; Christopher D. Coffey, 6020 Crestview, Indianapolis, Ind. 46202

[21] Appl. No.: 29,526

[22] Filed: Mar. 11, 1993

[51] Int. Cl.$^5$ ............................................. A61B 17/00
[52] U.S. Cl. ..................................... 606/228; 606/224
[58] Field of Search .............................. 606/224–231

[56] References Cited

U.S. PATENT DOCUMENTS

| | | | |
|---|---|---|---|
| 3,570,497 | 3/1971 | Lemole | 606/224 |
| 4,989,764 | 2/1991 | Hoffman et al. | 606/224 |
| 5,074,874 | 12/1991 | Yoon et al. | 606/224 |
| 5,123,913 | 6/1992 | Wilk et al. | 606/224 |
| 5,178,629 | 1/1993 | Kammerer | 606/224 |
| 5,207,694 | 5/1993 | Broomé | 606/228 |
| 5,222,976 | 6/1993 | Yoon | 606/228 |

*Primary Examiner*—Stephen C. Pellegrino
*Assistant Examiner*—Gary Jackson
*Attorney, Agent, or Firm*—Barnes & Thornburg

[57] ABSTRACT

A suture for use in MIS surgery and tying internally in a body cavity using graspers extending through trocars in the body wall, the suture comprising a length of suture material suitable for fastening body tissue within the body cavity, the length having opposite end portions, and gripping means attached to at least one of the end portions. The gripping means, which may be formed and shaped to facilitate engagement and movement by graspers, may be a soft, sponge-like body attached to the length end or an elongated body in the shape of a paddle attached to the length end for use by a grasper in the movement of a body organ.

9 Claims, 2 Drawing Sheets

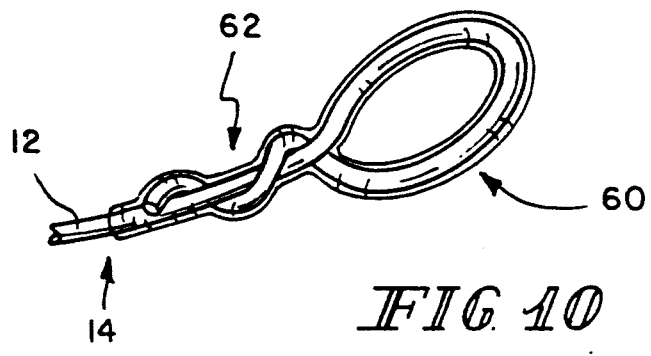
FIG. 10
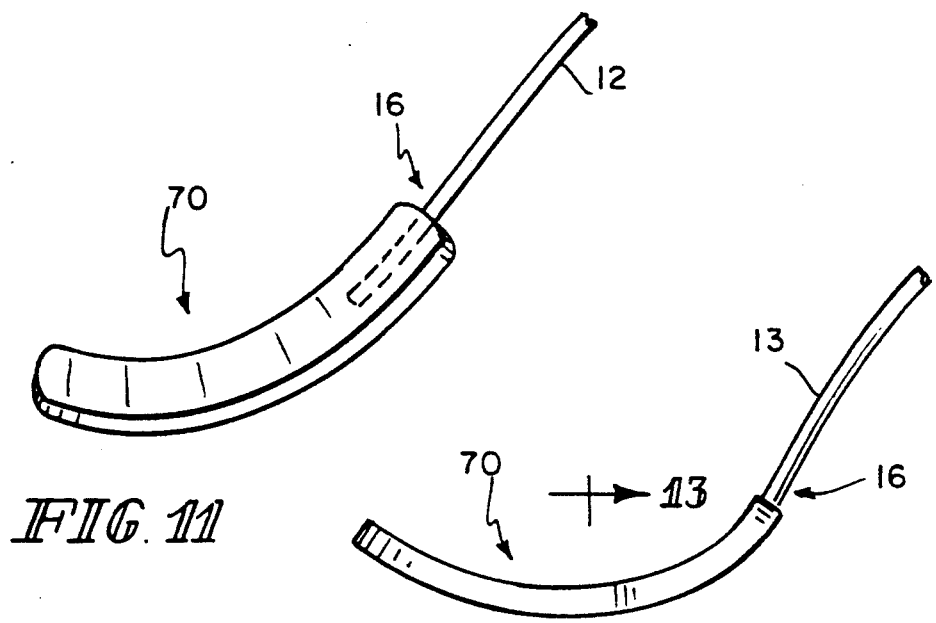
FIG. 11
FIG. 12
FIG. 13

SUTURE FOR USE IN ENDOSCOPIC SURGERY

BACKGROUND AND SUMMARY OF THE INVENTION

The present invention relates to sutures for use in laparoscopic/pelviscopic surgery, and more particularly to the provision of sutures which are more easily tied and secured in a body cavity using graspers extending through trocars in the body wall.

The present invention relates to suture tying or suture fastening in laparoscopic/pelviscopic surgery which is a rapidly growing field of surgery in this and other countries. Typically, a patient is anesthetized and placed on a surgery table for surgery. An initial very small opening, perhaps 12 mm in diameter, is made in the body wall for insertion of a scope or optic probe which will facilitate viewing inside the body cavity. In the case of the abdominal cavity, for instance, the cavity may be expanded by an insufflation process using carbon dioxide under pressure. This type of surgery is beginning to be well known as Minimally Invasive Surgery (MIS) or Less Invasive Surgery (LIS).

One of the well known problems with MIS or LIS is that the use of sutures is a very difficult task for many surgeons. The surgeon has to be able to tie a suture inside the body cavity using graspers which extend through trocars in the body wall. The surgeon has to do this tying while viewing the suture and the body tissue with which the suture is used on a television camera picking up the image through the scope or optic probe.

Many MIS or LIS procedures are accomplished today using very expensive disposable clip guns which apply titanium clips to various body conduits such as the cystic duct, artery or other blood vessel. Some of these clip guns may cost the hospital, for instance, more than $200 and up to as much as $280. These clip guns are so frail and intricate in design and made from plastic that they cannot be easily sterilized to be reusable after a surgery. They are simply loaded with a supply of, for instance, twenty clips to be used in a single MIS or LIS procedure and then disposed of with all of the other disposable equipment used in the procedure.

It is believed that more surgeons would use low-cost sutures and not use the more expensive titanium clips requiring the disposable clip guns in MIS or LIS if suture ligation was made easier inside the body cavity. In addition, many surgeons prefer the security of sutures over metal clips.

It is an object of the present invention, therefore, to provide a suture for use in MIS or LIS surgery and tying intracorporeally using graspers which extend through trocars in the body wall, the suture comprising a length of suture material suitable for fastening (approximating) body tissue within the body cavity. The suture length, of course, has opposite end portions. A gripping means is attached to at least one of the end portions of the suture length, the gripping means being formed and shaped to facilitate engagement and movement by the graspers conventionally used in MIS or LIS surgery to facilitate tying a knot in the suture length.

In one embodiment of the present invention, a needle will be attached (swedged on) to the other end portion of the suture length to facilitate penetration of the suture length through tissue, whereby the opposite end portions can then be tied by manipulating the gripping means and the needle.

Another object of the present invention is to provide such a gripping means which comprises a soft, sponge-like body attached to the suture length opposite end. This body may be generally elongated in the direction of the suture length to have a proximal end attached to an end portion of the length and a distal end extending away from the length. In another embodiment of the present invention, the body may be a wax-like or deformable material enclosing the suture end portion to be gripped by a grasper. This wax-like or deformable material may be made from a material which will be absorbable in the body cavity. The body may be impregnated with any suitable pharmaceutical material such as, for instance, an antibiotic agent.

In accordance with the present invention, the gripping means body is preferably of a diameter small enough to be placed through the body wall by passing through a cannula having an internal diameter in the range of 5 mm to 12 mm.

Another object of the present invention is to provide a ligation suture for use in tying off a body conduit such as the cystic duct, artery or other blood vessel inside a body cavity during MIS or LIS surgery procedures using graspers extending through trocars in the body wall, the suture comprising a length of suture material sufficiently long to accommodate the circumference of the targeted conduit and the knot to be tied, the length having opposite end portions. A gripping means is attached to each length end portion, the gripping means being formed to have a size larger in transverse cross section than the suture length cross section to facilitate gripping and controlled movement with the graspers.

The gripping means may comprise a body formed from a material more rigid than the suture material, and may be formed as an elongated body attached to the suture length. The elongated body may have a length greater than about three times its transverse cross sectional dimension. In some cases, the body may be shaped as a slightly curved paddle in the elongated direction for use in moving tissue deflecting an organ or encircling a structure to be ligated.

Further, the gripping means may be made of material or coated with material which is colored to be distinctive in the scope view or on the video screen.

Other objects and features of the present invention will become apparent as this description progresses.

BRIEF DESCRIPTION OF THE DRAWINGS

FIG. 10 is a view showing the suture length end portion made into a loop to facilitate gripping and coated with a stiffening material to hold the shape of the loop;

FIG. 11 is a fragmentary perspective view showing a slightly curved paddle-like gripping means;

FIG. 12 is an elevational view of the gripping means of FIG. 11; and

FIG. 13 is a sectional view taken along the lines 13—13 in FIG. 12.

DETAILED DESCRIPTION OF THE DRAWINGS

Figure 1:
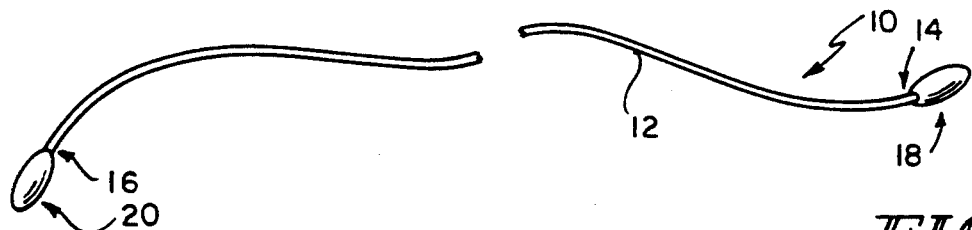
FIG. 1 is a view of a suture showing gripping means formed on the opposite ends of the length of suture.

Turning first to FIG. 1, it will be seen that a suture 10 is shown comprising a length 12 of suture material, the length 12 having opposite end portions 14, 16. Gripping means 18, 20 may be attached to each end portion 14, 16, respectively, to facilitate the gripping of the suture 10 ends by the typical jaw-like graspers conventionally used in MIS or LIS surgery. The illustrative gripping means 18, 20 may be formed in a variety of shapes and from a variety of materials to facilitate the gripping of the suture end portions 14, 16 by a conventional grasper. The illustrative gripping means 18, 20 may be, for example, formed from a wax-like or deformable material which may, for some surgery applications, be dissolvable or absorbable into the body if left in the body cavity. This type of material may even be impregnated with a medicant such as an antibiotic agent.

The gripping means 18, 20 shapes illustrated in FIG. 1 are somewhat elongated elliptical shapes, elongated in the direction of the length 12. Preferably, these gripping means 18, 20 will be of a cross sectional size such that they may be dropped into the body cavity through a 5 mm cannula extending into the body cavity through a trocar. It will be appreciated that, in a MIS procedure, access may be obtained to an abdominal body cavity through cannula extending through the body wall and having internal diameters ranging from, for instance, 5 mm up to about 12 mm. It is believed that an effective gripping means 18, 20 may be elongated even beyond that shown in FIG. 1 such that each gripping means is, perhaps, three to five times or even longer than its cross sectional dimension. Since the suture 10 will be used in MIS, and the gripping means 18, 20 will be viewed on a television screen or through a scope, the gripping means may preferably be fabricated from a material which will provide significant color contrast to the body tissues being observed so that they will be easily seen and used.

Figure 2:
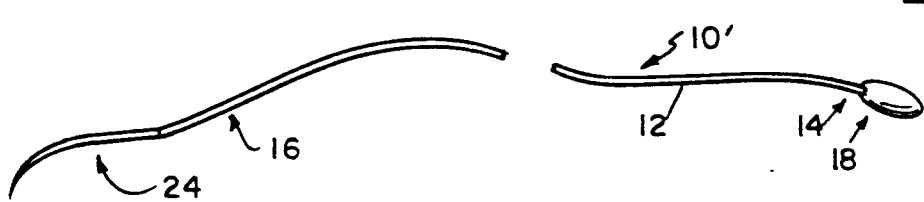
FIG. 2 is a suture showing a needle attached one end of the suture length and a gripping means attached to the opposite end of the suture length.

The object of the suture 10 shown in FIG. 1 is to provide the gripping means 18, 20 which can be easily seen and easily gripped and controlled and manipulated by the conventional graspers used in MIS surgery. The suture 10 may be used, for example, as a ligation suture to tie off a conduit such as the cystic duct in a gallbladder MIS procedure, referred to as a laparoscopic cholecystectomy. Most surgeons should be able to use conventional graspers and the gripping means 18, 20 to tie the suture 10 (tie a knot) after it is wrapped around a body conduit and to save the rather expensive cost of a clip applicator gun. The illustrated elliptical shape gripping means 18, 20 in FIGS. 1 and 2 is merely illustrative, and the shape may be varied to fit the applications. For instance, simple elongated cylinders or rectangular blocks may be used. Further, the nature of the suture is immaterial to the present invention. The gripping means of the present invention may be used with any type or size suture material. The length, diameter and characteristics will be selected by the surgeon.

FIG. 2 shows a suture 10' similar to the suture 10 shown in FIG. 1 except that a needle 24 is attached in a conventional manner to the end portion 16 of the suture length 12 so that the suture may be used to penetrate through tissue in the body cavity. In the use of the suture 10', graspers will be used to control and direct the needle 24 through the body tissue and then after the suture length 12 is penetrated through the body tissue to make the required suture, graspers may be used to control the needle 24 and the gripping means 18 to tie the suture after it is penetrated through the tissue.

Figure 3:
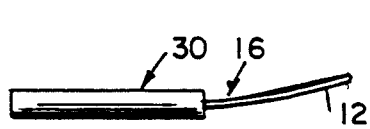
FIG. 3 is a fragmentary view showing an elongated gripping means attached to one end of a suture.
Figure 4:
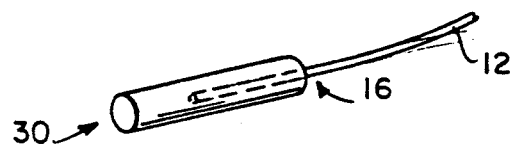
FIG. 4 is a fragmentary perspective view of the suture shown in FIG. 3 illustrating the elongated gripping means.

In FIG. 3, the suture length 12 end portion 16 is shown attached to an elongated cylindrically-shaped gripping means 30 which may illustratively be somewhat rigid, at least as compared to the suture length 12 to facilitate the gripping and controlled movement. As illustrated in FIG. 4, the end portion 16 of the suture length 12 may be molded or otherwise formed within the body of the gripping means 30. Typically, the gripping means 30, which may be made of a sponge-like or soft but somewhat stiff material for facilitating its graspability, may have a length greater than, for example, five times or even eight times its cross sectional diameter. A gripping means which is, for example, 4 mm in diameter, may have a length 20 mm or even 30 or 40 mm long. Such a gripping means may be inserted through a 5 mm cannula. In any event, it is believed that the gripping means 18, 20 in FIG. 1 and 30 in FIG. 4 may have a length greater than about three times its transverse cross sectional diameter and possibly even five to ten times its cross sectional diameter.

Figure 5:
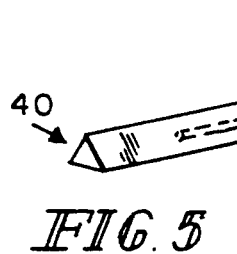
FIG. 5 is a fragmentary view of a suture showing an elongated gripping means attached to one end with the gripping means having a triangular cross sectional shape.
Figure 6:
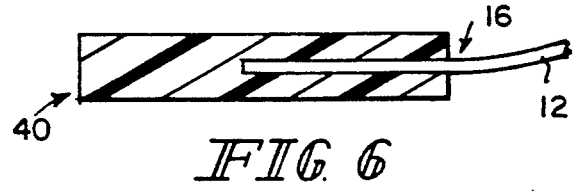
FIG. 6 is a fragmentary sectional view showing how the end of a suture length may be molded or embedded in a plastic or plastic-like gripping means.

In FIGS. 5 and 6, a gripping means 40 having a generally triangular cross sectional shape is shown attached to the end portion 16 of the suture length 12. The triangular cross sectional shape is believed to be advantageous for gripping and controlled movement by the jaws of a conventional grasper. It is believed that the edges of the triangular cross-section gripping means 40 will fit into the teeth on the upper or lower jaws of the grasper to be held securely when the grasper is closed. FIG. 6 suggests that the gripping means 40 may be molded or otherwise formed on the end portion 16 of the suture length 12. It will be appreciated that the suture end portion 16 may be inserted into a mold in which the plastic or plastic-like material of the gripping means 40 is injected.

Figure 7:
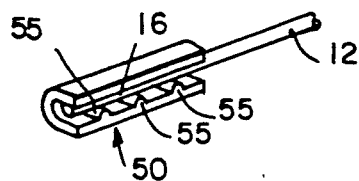
FIGS. 7, 8 and 9 are views illustrating how an elongated gripping means may be formed and attached by welding or other pressure deformation to attach the gripping means to the suture.
Figure 8:
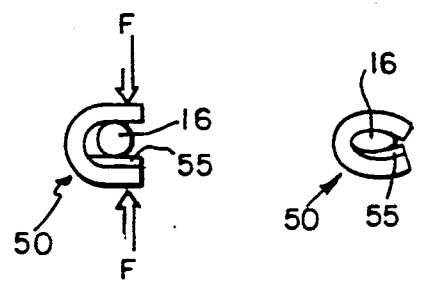
Figure 9:
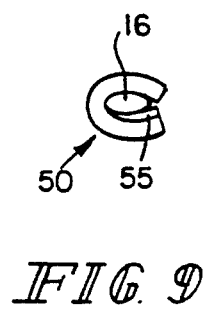

FIGS. 7, 8 and 9 show how a gripping means 50 may be clamped downwardly on an end portion 16 of a suture length 12 and welded or otherwise pressure formed and closed to capture the end portion. The illustrative gripping means 50 is shown to be an elongated member having a C-shaped cross section in FIG. 7 to receive the end portion 16. The gripping means 50 may have a plurality of ridges 55 as shown to grip suture end portion 16 when the C-shaped member is clamped with forces F as shown in FIG. 8 to produce the cross sectional shape shown in FIG. 9. Techniques for welding or joining plastic by the application of pressure and energy to capture another material, such as a suture, are well known.

The illustrative gripping means 18, 20, 30, 40 and 50 may be made from a variety of plastic or plastic-like materials which are suitable for use in surgery. They may be made from a sponge-like material or even a wax-like material to facilitate handling and grasping.

FIG. 10 shows a gripping means 60 which is formed on the end portion 14 of the suture length 12 by forming a loop as illustrated and then coating the loop and the end portion with a plastic-like material which will give the suture length end portion 14 some considerable rigidity such that the loop itself will facilitate gripping and control by the conventional grasper jaws. The coating material for the gripping means 60 may be somewhat stiff, but flexible to permit the loop to be moved through a 5 mm cannula.

FIGS. 11–13 show an elongated, paddle-like. gripping means 70 attached to the end portion 16 to serve as a gripping means for a grasper as discussed above and also to serve as a spatula or dull blade-like member for moving a body organ such as the cystic duct or for pushing behind a duct for suture tying.

What is claimed is:

1. A suture for use in MIS surgery and tying internally in a body cavity using graspers extending through trocars in the body wall, said suture comprising a length of suture material suitable for fastening body tissue within the body cavity, said length having opposite end portions, and gripping means attached to at least one of said end portions, said gripping means being formed and shaped to facilitate engagement and movement by graspers, said gripping means comprising a soft, sponge-like body attached to said length end.

2. The invention of claim 1 in which said body is generally elongated in the direction of said length to have a proximal end attached to an end portion of said length and a distal end extending away from said length.

3. The invention of claim 1 in which said gripping means comprises a body of deformable wax-like material enclosing said opposite end portion to be gripped by a grasper.

4. The invention of claim 3 in which said body is of a diameter small enough to be placed through the body wall by passing through a cannula having an internal diameter in the range of 5 to 12 mm.

5. A ligation suture for use in tying off a body conduit such as a cystic duct, artery or blood vessel inside a body cavity during MIS surgery procedures using graspers extending through trocars in the body wall, said suture comprising a length of suture material sufficiently long to accommodate the circumference of the targeted conduit and the knot to be tied, said length having opposite end portions, and gripping means attached to each length end portion, each of said gripping means being formed to have an elongated body of size larger in cross section than the suture cross section having a blunt configurators to facilitate gripping and controlled movement with the graspers inside the body.

6. The invention of claim 5 in which said gripping means comprises a body formed from a material more rigid than said suture length.

7. The invention of claim 5 in which said gripping means comprises an elongated body attached to said suture length, said elongated body having a length greater than about three times its transverse cross sectional dimension.

8. The invention of claim 5 in which said gripping means comprises an elongated body in the shape of a paddle for use by a grasper in the movement, of a body organ.

9. The invention of claim 8 in which the elongated body is an elongated, relatively flat body having a proximal end attached to said opposite end and a distal end extending away from said suture length, said body being slightly curved about a transverse axis.

* * * * *